United States Patent
Pak et al.

(10) Patent No.: US 9,958,432 B2
(45) Date of Patent: May 1, 2018

(54) CELLULAR CIS-CO-CULTURE SYSTEMS FOR ANALYSIS

(71) Applicant: Lynx Biosciences, Inc., San Diego, CA (US)

(72) Inventors: Chorom Pak, Madison, WI (US); Edmond Wai Keung Young, Toronto (CA); Natalie Callander, Madison, WI (US); David James Beebe, Madison, WI (US); Shigeki Miyamoto, Madison, WI (US)

(73) Assignee: LYNX BIOSCIENCES, INC., San Diego, CA (US)

( * ) Notice: Subject to any disclaimer, the term of this patent is extended or adjusted under 35 U.S.C. 154(b) by 0 days. days.

(21) Appl. No.: 14/491,701

(22) Filed: Sep. 19, 2014

(65) Prior Publication Data

US 2015/0087006 A1 Mar. 26, 2015

Related U.S. Application Data

(60) Provisional application No. 61/880,642, filed on Sep. 20, 2013.

(51) Int. Cl.
| | |
|---|---|
| *C12N 5/07* | (2010.01) |
| *C12Q 1/02* | (2006.01) |
| *G01N 33/50* | (2006.01) |
| *G01N 33/543* | (2006.01) |
| *G01N 33/574* | (2006.01) |
| *C12M 3/06* | (2006.01) |
| *B01L 3/00* | (2006.01) |

(52) U.S. Cl.
CPC ......... *G01N 33/5008* (2013.01); *C12M 23/16* (2013.01); *G01N 33/5044* (2013.01); *G01N 33/54366* (2013.01); *G01N 33/57426* (2013.01); *B01L 3/502761* (2013.01); *B01L 2200/0647* (2013.01); *B01L 2300/0864* (2013.01); *B01L 2300/0867* (2013.01); *B01L 2400/0472* (2013.01); *G01N 2500/04* (2013.01)

(58) Field of Classification Search
CPC ........... G01N 33/5008; G01N 33/5044; G01N 2500/04
USPC .................................................. 435/29, 347
See application file for complete search history.

(56) References Cited

U.S. PATENT DOCUMENTS

2003/0109042 A1 5/2003 Wu et al.
2009/0117653 A1 5/2009 Kirshnir et al.

OTHER PUBLICATIONS

Yanamandra et al. Tipifarnib and Bortezomib are Synergistic and Overcome Cell Adhesion-Mediated Drug Resistance in Multiple Myeloma and Acute Myeloid Leukemia; Clinical Cancer Research, vol. 12, No. 2 (2006) pp. 591-599.*
Souto et al. Model for Human Skin Reconstrcuted in Vitrocomposed of Associated Dermis and Epidermis; Sao Paulo Medical Journal, vol. 24, No. 2 (2006) pp. 71-76.*
Zlei et al. Characterization of In Vitro Growth of Multiple Myeloma Cells; Experimental Hematology, vol. 35 (2007) pp. 1550-1561.*
Pak et al. Microfluidic Platform Enabling Primary Multiple Myeloma Mono- and Cis-Co-Culture Analysis; 54th ASH Annual Meeting and Exhibition, Abstract (Dec. 8, 2012), downloaded from https://ash.confex.com/ash/2012/webprogram/Paper53291.html on Nov. 18, 2015.*
Duffy et al., "Rapid Prototyping of Microfluidic Systems in Poly(dimethylsiloxane)." Anal Chem. Dec. 1, 1998; 70 (23):4974-84.
Hartigan et al., "A K-Means Clustering Algorithm" Journal of the Royal Statistical Society. Series C (Applied Statistics) 1979, 28(1):100-108.
Kim et al., "Macrophages and mesenchymal stromal cells support survival and proliferation of multiple myeloma cells." Br J Haematol. Aug. 2012; 158(3):336-46.
Kurita et al., "Maximum likelihood thresholding based on population mixture models." Pattern Recognition 1992, 25 (10): 1231-1240.
Lippert et al., "Current status of methods to assess cancer drug resistance." Int J Med Sci. Mar. 23, 2011; 8(3):245-53.
Markovina et al., "Bortezomib-resistant nuclear factor-kappaB activity in multiple myeloma cells." Mol Cancer Res. Aug. 2008; 6(8):1356-64.
McLachlan et al., "Finite Mixture Models." John Wiley & Sons Inc. 2000.
Munshi et al., "Consensus recommendations for risk stratification in multiple myeloma: report of the International Myeloma Workshop Consensus Panel 2." Blood. May 5, 2011; 117(18):4696-700.
Paguirigan et al., "Microfluidics meet cell biology: bridging the gap by validation and application of microscale techniques for cell biological assays." Bioessays. Sep. 2008; 30(9):811-21.
Petricoin et al., "Clinical proteomics: translating benchside promise into bedside reality." Nat Rev Drug Discov. Sep. 2002; 1(9):683-95.
Suggitt et al., "50 years of preclinical anticancer drug screening: empirical to target-driven approaches." Clin Cancer Res. Feb. 1, 2005; 11(3):971-81.
Ugurel et al., "In vitro drug sensitivity predicts response and survival after individualized sensitivity-directed chemotherapy in metastatic melanoma: a multicenter phase II trial of the Dermatologic Cooperative Oncology Group." Clin Cancer Res. Sep. 15, 2006; 12(18):5454-63.

(Continued)

*Primary Examiner* — Scott Long
*Assistant Examiner* — Paul Martin
(74) *Attorney, Agent, or Firm* — Cooley LLP

(57) ABSTRACT

The invention relates to systems and methods for studying patient cancer samples in cis-co-culture with stromal cells from the same patient. For example, the invention provide systems and methods for testing therapeutic agents in vitro in an environment that simulates an in vivo environment to identify agents that are therapeutically effective for the patient.

21 Claims, 21 Drawing Sheets

(56) References Cited

OTHER PUBLICATIONS

Xia et al., "Soft Lithography" Annual Review of Materials Science, Aug. 1998, 28:153-184.
Young et al. "Microscale functional cytomics for studying hematologic cancers." Blood. Mar. 8, 2012; 119(10):e76-85.
Zdzisińska et al., "A comparison of cytokine production in 2-dimensional and 3-dimensional cultures of bone marrow stromal cells of multiple myeloma patients in response to RPMI8226 myeloma cells." Folia Histochem Cytobiol. 2009; 47(1):69-74.

* cited by examiner

CELLULAR CIS-CO-CULTURE SYSTEMS FOR ANALYSIS

The present application claims priority to U.S. Provisional Patent Application Ser. No. 61/880,642, filed Sep. 20, 2013, the disclosure of which is herein incorporated by reference in its entirety.

STATEMENT REGARDING FEDERALLY-SPONSORED RESEARCH OR DEVELOPMENT

The present subject matter was partially supported by the National Institute of Health (NIH) under Agency Grant Numbers 1R01CA155192, and R01CA081065. The United States government has certain rights in the invention.

FIELD OF INVENTION

The invention relates to systems and methods for analyzing patient tissue samples in cis-co-culture (e.g., within a microfluidic environment).

BACKGROUND

Hematological malignancies account for a considerable amount of new cancer diagnoses. For example, multiple myeloma (MM) is a universally fatal disease, comprising 15% of hematological malignancies and 1% of all cancers. It has a median survival of 5-7 years from diagnosis. While newer drugs, such as the proteasome inhibitor bortezomib, have increased response to therapy, resistance and relapse still remain a key concern. Therefore, there is a need to understand the mechanism(s) of drug resistance.

SUMMARY

The invention relates to systems and methods for analyzing patient cancer samples in cis-co-culture (e.g., within a microfluidic environment). For example, provided herein are systems and methods that permit culturing of target cells (e.g., cancer cells) from a patient along with other cells (e.g., stromal cells) so as to mimic conditions in vivo to allow for analysis of the target cells in vitro. Analysis includes, but is not limited to, testing cells for chemosensitivity or chemoresistance and screening of candidate therapeutic agents. In some embodiments, cells are isolated in a microfluidic device that facilitates culturing, isolation, manipulation, detection, and/or analysis. In some embodiments, the cells are cultured on or in any device (e.g., directly or indirectly on a surface, in suspension, or any other desired method). The cis-co-cultured cells may be cultured physically together or physically separated (e.g., in fluid communication whether together or separated).

Culturing of cancer cells or cancer stem cells is useful for assessing the type of cancer present in a patient and characterizing that cancer. For example, cultured cancer cells from a patient can be used in proteomic analyses to assess the effectiveness of certain drugs in treating that patient. Petricoin E F et al.: "Clinical proteomics: translating benchside promise into bedside reality" *Nat Rev Drug Discov.* 2002 September; 1(9): 683-95. In another example, multiple myeloma cells from a patient can be cultured and assayed for NF-κB nuclear translocation after exposure to a variety of conditions. Young, E W et al.: "Microscale functional cytomics for studying hematologic cancers" *Blood.* 2012 Mar. 8; 119(10).

However, there are several limitations with conventional systems for functional cell assays. For example, standard in vitro models do not provide conditions that closely mimic in vivo conditions. Specifically, the cancer cells in an in vivo environment are influenced by neighboring cells (e.g., stromal cells), extracellular matrix, and systemic factors (e.g., cytokines, hormones). Paquirigan, A L et al.: "Microfluidics meet cell biology: bridging the gap by validation and application of microscale techniques for cells biological assays" *Bioessays.* 2008 September; 30(9): 811-21.

Another limitation with conventional systems for functional cell analysis is the large amount of required biological starting material from patients. For example, electrophoretic mobility shift assays (EMSAs) that detect transcription factor-DNA interactions typically require at a minimum $10^5$ or $10^6$ cells per condition from the patient. Markovina, S et al.: "Bortezomib-resistant nuclear factor-kappaB activity in multiple myeloma cells" *Mol Cancer Res.* 2008 August; 6(8): 1356-64. This amount of cells may not be obtainable from some patients. Young, E W et al.: "Microscale functional cytomics for studying hematologic cancers" *Blood.* 2012 Mar. 8; 119(10).

One further limitation with conventional systems for functional cell analysis is that many such assays (e.g., EMSAs) rely on population averages rather than single-cell data. Id. Population level readings can mask valuable data that might be available in single-cell assays. Id. An additional problem with conventional system for functional cell analysis is that enrichment for a specific cell type is often used. Artificial enrichment for a specific cell type (e.g., bone marrow stromal cells) reduces the similarity of a given cell culture system to the in vivo system it mimics.

Provided herein are systems and methods for efficient and effective culturing and analysis of cells. In some embodiments, the present invention provides systems and methods for patient-specific analysis of pharmaceutical agent effectiveness.

In some embodiments, the invention provides a device (e.g., comprising a solid support structure) for cell culture. In some embodiments, this device comprises distinct locations that are fluidically connected through channels. With this support structure, target cells from a patient are cultured in the same fluidic milieu as cells of different types from the same patient, in some embodiments, without allowing the different cell types to physically mingle with the target cells. This type of cell culture allows for a target cell to be cultured in an environment that is more similar to the patient-specific in vivo environment than mono-culture or co-culture with different cell types from other patients (trans-co-culture), resulting in accurate assessment of actual and predicted response to an agent.

In some embodiments, the present invention provides a more accurate method and system for replicating in vivo environments than traditional cell culture. Traditional co-culture methods and systems use artificial enrichment of a specific cell type in the stroma, such as bone marrow stromal cells. In some embodiments, the invention provides a cellular co-culture method that avoids this enrichment. The invention provides systems and methods to preserve stromal mononuclear cells present in bone marrow aspirates obtained from individual patients. In some embodiments, a heterogeneous mixture of stromal cell types is co-cultured with target patient cells to provide an accurate in vitro replication of the in vivo environment. It should be understood that the target patient cells described herein are not necessarily a pure isolated target cell or population of target cells, but instead includes, unless specified otherwise, populations of cells enriched for the target cell relative to the source of the cell found in nature (e.g., enriched 2-fold or more, 3-fold or more, 5-fold or more, 10 fold or more, etc.; e.g., wherein the target cell represents greater than 50%, greater than 60%, greater than 70%, greater than 80%, greater than 90% of the cell types in the population). As such, target cells may be present in a population of cells comprising non-target cells. Likewise, stromal cells populations, as used herein, may comprise non-stromal cells (e.g., cancer cells), but unless specified otherwise are either as harvested from a subject or are enriched for stromal cells relative to the source of the cells found in nature.

In some embodiments, the invention provides a method for cellular analysis comprising a) placing target cells from a patient on or in a device (e.g., solid support); b) placing stromal cells from the same patient in fluidic connection with the target cells (e.g., placing stromal cells from the same patient in fluidic connection with the target cells via diffusion ports that are not large enough for the target or stromal cells to cross or that otherwise restrict the location of the cells based on a physical parameter); c) contacting the target cells and/or stromal cells with an agent; and d) measuring an effect or lack of effect of the agent on the target cells and/or stromal cells. In some embodiments, the target cells are cancer cells such as hematological cancer cells. In some embodiments, the target cells are Hodgkin's lymphoma, non-Hodgkin's lymphoma, lymphoblastic leukemia (acute and chronic), or multiple myeloma cells. In some embodiments, the device is or comprises a solid support such as a chip, dish, bead, scaffold, or gel. In some embodiments, the device is configured for suspension culture or other cell culture techniques. In some embodiments, the agent is a drug. In some embodiments, the stromal cells are bone marrow stromal cells. In some embodiments, the invention relates to the determination of which drug or drugs to administer to a patient.

In some embodiments, the invention provides a method for cellular analysis comprising co-culturing target cells and non-target cells (e.g., stromal cells) (e.g., from the same patient); contacting the cells with an agent; and determining an effect or lack of effect of the agent on the target cells and/or non-target cells. In some embodiments, the cells are cultured such that the effect of the agent on the target cells is different than an effect the agent has on target cells cultured in the absence of the non-target cells.

In some embodiments, the method further comprises treating a subject (e.g., the patient from which the target cells were derived) with an agent identified by the methods above as having a therapeutic effect on the target cells or non-target cells.

In some embodiments, the invention provides a cell culture method for simulation of patient environment comprising one or more or all of the steps of: a) harvesting target cells and stromal cells from the same patient; b) sorting the cells based on the presence or absence of a marker; c) placing the target cells on one side of a barrier with ports that are not large enough for the target or stromal cells to cross; d) placing the stromal cells on another side of the barrier; e) ensuring that the stromal cells and target cells are in fluid connection across the barrier; f) contacting the target cells with an agent; and g) determining whether the agent had an observable effect on the target cells. In some embodiments, a further step of quantification of the observable effect is performed. In some embodiments, the target cells are hematological cancer cells such as Hodgkin's lymphoma, non-Hodgkin's lymphoma, lymphoblastic leukemia (acute and chronic), or multiple myeloma cells. In some embodiments, the agent is a drug and the observable effect on the target cells is used to determine which drug or drugs to administer to the patient.

In some embodiments, provided herein are methods for cellular analysis comprising: a) placing target cells from a patient on or in a device (e.g., solid support); b) placing non target cells (e.g., stromal cells) from the same patient in contact with, in culture with, or in fluidic connection with the target cells; c) contacting the target cells and/or non-target cells with an agent; and d) measuring an effect or lack of effect of the agent on the target cells and/or non-target cells. In some embodiments, the placing of non-target cells comprises placing the stromal cells in a portion of the device not occupied by the target cells (e.g., comprises placing non-target cells via diffusion ports that are not large enough for the target or stromal cells to cross).

Any cells may be used. However, in some embodiments, the target cells are cancer cells. In some embodiments, the cancer cells are hematological cancer cells. In some embodiments, the hematological cancer cells are multiple myeloma cells. In some embodiments, other hematological cancer cells such as Hodgkin's lymphoma, non-Hodgkin's lymphoma, or lymphoblastic leukemia (acute and chronic) are used instead of multiple myeloma cells. In some embodiments, the non-target cells are stromal cells, such as bone marrow stromal cells.

Any type of culturing device may be used. In some embodiments, the culturing device is a solid support that is a chip, dish, bead, scaffold, or gel.

Any type of agent may be used. In some embodiments, the agent is a drug. In some embodiments, the agent is a chemotherapeutic agent. In some embodiments, the agent is a candidate chemotherapeutic agent (i.e., an agent suspected of being a chemotherapeutic agent, but not yet proven to be a chemotherapeutic agent (e.g., against the target cell)).

In some embodiments, the effect of the drug on the target cells is used to determine which therapies (e.g., drug(s)) to administer to the patient. For example, in some embodiments, the method further comprises the step of administering an agent, identified as having therapeutic benefit against the target cell or non-target cell, to the patient. In some embodiments, the method further comprises the step of reporting to a health care worker an identity of an agent likely to be therapeutically effective for said patient (e.g., a service lab conducts tests on cells received from a health care facility, obtains results, and reports or displays results back to the health care facility so that the health care worker can administer a therapeutically effective agent to the patient).

In some embodiments, provided herein are methods (e.g., conducted by health care workers) comprising: having a sample tested (e.g., by a third party service laboratory), using any of the methods described herein, and administering to a patient an agent identified as having therapeutic benefit against the target cells from the patient.

In some embodiments, provided herein are cell culture methods comprising one or more or all of the steps of: a) harvesting target cells and non-target cells (e.g., stromal cells) from a patient or receiving target cells and non-target cells harvested from a patient (e.g., a service lab receiving cells from a health care facility that obtained the cells from a patient); b) optionally enriching or sorting the target cells based on the presence or absence of a marker; c) optionally manipulating the enriched or sorted target cells, wherein the manipulating involves one or more of: labeling the target cells, genetically altering the target cells, preserving the target cells, culturing the target cells, and combining the target cells with other cells; d) placing the target cells in culture (e.g., on a region of the device; on one side of a barrier with ports that are not large enough for the target or non-target cells to cross); d) placing the non-target cells in culture (e.g., on the same or another region of the device; on another side of the barrier); e) optionally, ensuring that the non-target cells and target cells are in fluid connection with one another (e.g., across the barrier); f) contacting the target cells and/or non-target cells with an agent; and g) determining whether the agent had an observable effect on the target cells and/or non-target cells. In some embodiments, the method further comprises the step of quantifying the observable effect.

In some embodiments, provided herein are systems for patient-specific in vitro analysis comprising: a) a device (e.g., a solid support); b) cultured target cells (e.g., multiple myeloma cells) from a patient on or in a region of the device; and c) cultured non-target co-culture cells (e.g., stromal cells such as bone marrow stromal cells) from the same patient on or in the device. In some embodiments, the co-cultured cells are in a separate region of the solid support than the target cells. In some embodiments, the system further comprises a pharmaceutical agent or candidate pharmaceutical agent in contact with the target cells. In some embodiments, the solid support comprises two or more separate regions that are fluidically connected through channels with dimensions no greater than 300 µm wide and 70 µm deep. In some embodiments, the solid support is a chip, dish, bead, scaffold, or gel.

Also provided herein are uses of any of the described system, for example, to identify a therapeutically effective agent for a patient, to identify drug resistance, to validate a candidate therapeutic agent, or any other desired purpose.

Further provided herein are methods of determining chemosensitivity or chemoresistance of a cell or cell population, comprising: collecting data associated with an effect of a drug on target cells and stromal cells harvested from a subject that have been co-cultured; and analyzing said data to determine chemosensitivity or chemoresistance of said target cells and/or said stromal cells to said drug.

DESCRIPTION OF FIGURES

In FIG. 1A, the chip comprises a central well connected to 2 side chambers, via diffusion channels. The cells are seeded through the inlet ports and fluid is passively flown from the inlet to outlet ports. In some embodiments, the central well has low wall shear stress at the bottom of the well to retain settled non-adherent cells. In this figure, multiple myeloma (MM) cells are used illustratively, but many other types of cells can be used instead. In this illustrative example, the central well comprises CD138+ multiple myeloma cells and the side chambers comprise CD138− mononuclear cells. The diffusion ports (also referred to as "channels") allow media and soluble factors to diffuse among the central well and the side chambers, but the diffusion ports are not tall enough for cells to pass through. In some embodiments, the diffusion channels are 100 µm wide and 20 µm deep. FIG. 1B shows a more three dimensional view of an embodiment of the device of FIG. 1A with a pipette tip shown above the device.

FIG. 2a shows results for patient 314. FIG. 2l shows results for patient 398. FIG. 2r shows results for patient 447. Patient 329 was refractory to bortezomib at the time of the cell harvest. When the patient's MM cells were grown in co-culture with the patient's own mononuclear cells, the MM cells appeared resistant to bortezomib. However, when the MM cells were grown in mono-culture, they exhibited less resistance. In this way, the cis-co-culture method described herein predicted resistance of MM cells to bortezomib more accurately than mono-cultured MM cells. Patient 316 was refractory to bortezomib at the time of the cell harvest. When the patient's MM cells were grown in co-culture with the patient's own mononuclear cells, the MM cells appeared resistant to bortezomib. However, when the MM cells were grown in mono-culture, they exhibited less resistance. In this way, the cis-co-culture method described herein predicted resistance of MM cells to bortezomib more accurately than mono-cultured MM cells. Patient 318 was refractory to bortezomib at the time of the cell harvest. When the patient's MM cells were grown in co-culture with the patient's own mononuclear cells, the MM cells appeared resistant to bortezomib. However, when the MM cells were grown in mono-culture, they exhibited less resistance. In this way, the cis-co-culture method described herein predicted resistance of MM cells to bortezomib more accurately than mono-cultured MM cells. Patient 315 was sensitive to bortezomib at the time of the cell harvest. When the patient's MM cells were grown in co-culture with the patient's own mononuclear cells, the MM cells exhibited a similar response to bortezomib as when the cells were grown in mono-culture. In this way, the cis-co-culture method described herein predicted sensitivity of MM cells to bortezomib as well as mono-cultured MM cells. Patient 344 was sensitive to bortezomib at the time of the cell harvest. When the patient's MM cells were grown in co-culture with the patient's own mononuclear cells, the MM cells exhibited a similar response to bortezomib as when the cells were grown in mono-culture. In this way, the cis-co-culture method described herein predicted sensitivity of MM cells to bortezomib as well as mono-cultured MM cells. Patient 345 was sensitive to bortezomib at the time of the cell harvest. When the patient's MM cells were grown in co-culture with the patient's own mononuclear cells, the MM cells exhibited a similar response to bortezomib as when the cells were grown in mono-culture. In this way, the cis-co-culture method described herein predicted sensitivity of MM cells to bortezomib as well as mono-cultured MM cells.

FIG. 3 shows a summary graph of the cluster analysis, differentiating responsive cells from non-responsive cells.

FIG. 4 shows a graph of the data, demonstrating the sensitivity/resistance profile.

DEFINITIONS

Figure 1A:
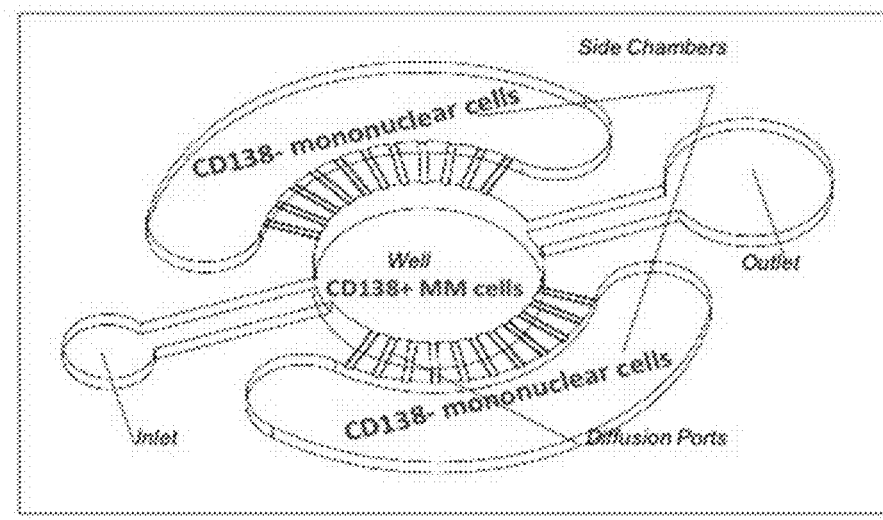
FIG. 1A-1B. Chip design. In some embodiments, the present invention provides a chip for culturing cells and a method using the chip.

As used herein, the term "cell culture" or "culture" refers to the process by and conditions under which cells or tissue is maintained under artificial conditions for a short or long time outside of the organism from which it was originally extracted. "Cell culture" is a generic term that may also encompass the cultivation of prokaryotes and eukaryotes. The term "mono-culture" refers to a type of cell culture in which all cultured cells are the same type. Culturing, as used herein, can include, but does not require, cell division of cultured cells.

As used herein, the term "cellular co-culture" or "co-culture" refers to the process by which a mixture of two or more different cell types are grown together or the mixture itself. The term "trans-co-culture" refers to the process or system of growing together different cell types from different patients. For example, "trans-co-culture" describes a system in which Patient A's cancer cells are cultivated with Patient B's stromal cells. The term "cis-co-culture" refers to the process or system of growing or maintaining together different cell types from the same patient. For example, "cis-co-culture" describes a system in which Patient A's cancer cells are cultivated with Patient A's stromal cells. For either type of co-culture, the different cell types can be harvested at different times and stored for different lengths of time. In some forms of "cis-co-culture", cells of one type are frozen or cultured for several days before cells of a different type are collected and the "cis-co-culture" is assembled.

As used herein, the term "cancer" refers to any hyper-proliferative disease that includes a malignancy characterized by deregulated or uncontrolled cell growth. Cancers of virtually every tissue are known. Examples of cancers include, but are not limited to carcinoma, lymphoma, blastema, sarcoma, and leukemia or lymphoid malignancies. The term "hematological cancer" or "hematological malignancy" refers to any malignancy associated with cells in the bloodstream, bone marrow, or lymphoid system. Hematological cancers include but are not limited to Hodgkin's lymphoma, non-Hodgkin's lymphoma, lymphoblastic leukemia (acute and chronic), or multiple myeloma. The term "multiple myeloma" refers to a disseminated malignant neoplasm of plasma cells which is characterized by multiple bone marrow tumor foci and widespread osteolytic lesions. The term "Hodgkin's lymphoma" refers to cancer originating from the lymphocytes and characterized by the orderly spread of disease from one lymph node group to another and by the development of systemic systems with advanced disease.

As used herein, the term "microfluidic" refers to a device or system through which materials, particularly fluid born materials such as liquids, are transported on a microscale, and in some embodiments on a nanoscale. "Microfluidic systems" are systems arranged to deliver small amounts of fluid, for example, less than 1 ml of fluid.

The term "agent", as used herein, includes a compound that induces a desired pharmacological and/or physiological effect. The term also encompass pharmaceutically acceptable and pharmacologically active ingredients of those compounds including but not limited to their salts, esters, amides, prodrugs, active metabolites and analogs. This term includes the active agent per se, as well as its pharmaceutically acceptable, pharmacologically active salts, esters, amides, prodrugs, metabolites and analogs. The term "agent" is not to be construed narrowly but extends to small molecules, proteinaceous molecules such as peptides, polypeptides and proteins as well as compositions comprising them, and genetic molecules, such as RNA, DNA and their mimetics and chemical analogs, as well as cellular agents. The term "agent" includes a cell which is capable of producing and secreting the polypeptides referred to herein as well as a polynucleotide comprising a nucleotide sequence that encodes this polypeptide. Thus, the term "agent" extends to nucleic acid constructs including vectors such as viral or non-viral vectors, expression vectors and plasmids for expression in and secretion in a range of cells. The term "agent" includes plasma or other blood products.

As used herein, the term "drug" refers to any substance intended for use in the diagnosis, cure, mitigation, treatment, or prevention of disease, or to affect the structure or function of? the body. The term "drug" refers to a variety of substances including but in no way limited to afatinib, denosumab, lenalidomide, trametinib, dabrafenib, radium Ra 223 dichloride, erlotinib, ado-trastuzumab emtansine, acetylsalicylic acid, bergamottin, dihydroxybergamottin, paradicin-A, pomalidomide, doxorubicin hydrocholoride, bevacizumab, bortezomib, docetaxel, aziridines, streptozotocin, cytarabine, podophyllotoxin, actinomycin, cyclophosphamide, methotrexate, 5-fluorouracil, vinblastine, dacarbazine, and prednisolone.

As used herein, the term "patient" refers to animals, including mammals, preferably humans.

As used herein, the term "in vivo" means within a living organism and "ex vivo" means outside of a living organism. As used herein, the term "in vitro" refers to operations carried out in an artificial system.

As used herein, the term "fluid connection" or "fluidically connected" or similar means that a system allows fluid to flow between two or more elements. Two reservoirs can be physically isolated by a barrier but fluidically connected by channels that allow fluid to flow between then.

As used herein, the term "channel" or "diffusion pore" refers to pathway in or through a medium that allows for movement of fluids such as liquids or gases, which may contain soluble factors. The term "microchannel" refers to a channel having cross-sectional dimensions in the range of about 1.0 µm to 500 µm, preferably between about 15 µm and 200 µm.

As used herein, the term "target cell" refers to a cell which is extracted from a patient, isolated (e.g., to purity or via enrichment in a cell population), and analyzed. Target cells can be isolated using a variety of techniques including but not limited to beads and columns. Sometimes, a cell contains a distinct marker such as CD138 which facilitates cell isolation or enrichment. "Target cell" can refer to cells of many different types such as Hodgkin's lymphoma, non-Hodgkin's lymphoma, lymphoblastic leukemia (acute and chronic), or multiple myeloma cells.

As used herein, the term "stroma" or "stromal cell" refers to connective tissue of an organ such as the endometrium, prostate, or bone marrow. Stromal cells include but are not limited to fibroblasts, macrophages, monocytes, endothelial cells, and pericytes. As an illustrative example, stromal cells in the bone marrow are not directly involved in hematopoiesis. Instead, bone marrow stromal cells provide a proper microenvironment for hematopoiesis by the bone marrow parenchymal cells. For example, bone marrow stromal cells generate colony stimulating factors.

As used herein, the term "solid-support" refers to non-gaseous, non-liquid material having a surface. For example, solid-supports can be flat such as glass, silicon, metal, plastic, or composite; or they can be in the form of a bead such as silica gel, controlled pore glass, magnetic or cellulose bead; or they can be pins such as pins suitable for combinatorial synthesis or analysis.

As used herein, the term "chamber" or "well" refers to any structure in which volumes of fluid can be contained.

DETAILED DESCRIPTION

Hematological malignancies account for a considerable amount of new cancer diagnoses. For example, multiple myeloma (MM) is a universally fatal disease, comprising 15% of hematological malignancies and 1% of all cancers. It has a median survival of 5-7 years from diagnosis. While newer drugs, such as the proteasome inhibitor bortezomib, have increased response to therapy, resistance and relapse still remain a key concern. Therefore, there is a need to understand the mechanism(s) of resistance to cancer-treating agents. Ideally, this is accomplished in a patient-specific manner.

Figure 1B:
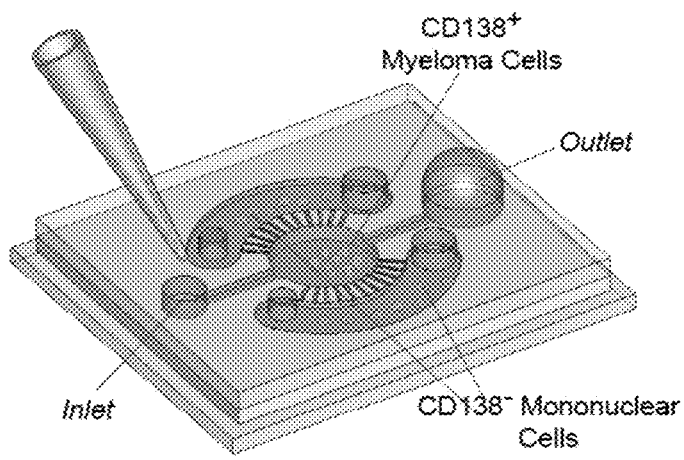

One approach for patient-specific resistance analysis is to directly examine biological responses of patient target cancer cells in the presence of their own stromal cell components ("cis-co-culture" or "intra-patient" analysis, FIG. 1) under different drug conditions. While "trans-co-culture" (or "inter-patient" analysis) in which cancer cells and stromal elements are derived from different patients or people has been reported before, the cis-co-culture concept is unique to this application (FIG. 1).

The invention described herein provides, in some embodiments, microfluidics-based microchannel platforms for analysis of samples in mono- and/or cis-co-culture. Many hematologic cancers can also be treated with the technology described herein. In some embodiments, the present invention is useful in assessment of and treatment of Adult Acute Lymphoblastic Leukemia, Childhood Acute Lymphoblastic Leukemia, Adult Acute Myeloid Leukemia, Childhood Acute Myeloid Leukemia, Chronic Lymphocytic Leukemia, Chronic Myelogenous Leukemia, Hairy Cell Leukemia, AIDS-Related Lymphoma, Cutaneous T-Cell Lymphoma, Adult Hodgkin Lymphoma, Childhood Hodgkin Lymphoma, Hodgkin Lymphoma During Pregnancy, Mycosis Fungoides, Adult Non-Hodgkin Lymphoma, Childhood Non-Hodgkin Lymphoma, Non-Hodgkin Lymphoma During Pregnancy, Primary Central Nervous System Lymphoma, Sézary Syndrome, Cutaneous T-Cell Lymphoma, Waldenström Macroglobulinemia, Chronic Myeloproliferative Disorders, Langerhans Cell Histiocytosis, Multiple Myeloma/Plasma Cell Neoplasm, Myelodysplastic Syndromes, and Myelodysplastic/Myeloproliferative Neoplasms. In some embodiments, cells of these cancer types can be analyzed in an accurate in vitro system using the technology described herein.

In a first step, cells are isolated based on one or more cell-specific markers by affinity binding. For example, in some embodiments, CD138 is used as a marker to sort for patient myeloma cells from bone marrow aspirates. These patient myeloma cells are seeded into a device (e.g., FIGS. 1a and b) comprising a central well comprising a well for retaining a suspension of target patient cells. Next, patient stromal cells are isolated and seeded into one or more side chambers. In some embodiments, CD138-non-cancerous stromal mononuclear cells are seeded into each side chamber. While some embodiments use patient myeloma cells as target cells, other embodiments Hodgkin's lymphoma, non-Hodgkin's lymphoma, lymphoblastic leukemia (acute and chronic), or other hematological cancer cells as target cells.

In some embodiments, each side chamber communicates fluidically with the central well via diffusion ports (also referred to as "channels") that are large enough for media and soluble factors to diffuse across and small enough to prevent or restrict cells and larger insoluble matter from crossing. In some embodiments, the diffusion ports have dimensions no larger than 300 µm wide and 60 µm deep. In some embodiments, the diffusion ports have a width of 90-110 µm and a depth of 50-70 µm. In some embodiments, the central well contains the stromal cells and the side chambers contain the target cells. In further embodiments, the chambers are instead configured such that there are no central or side wells, and instead, the chambers are spread over the device in a symmetrical or asymmetrical pattern. In some embodiments, the chambers are positioned (e.g., with varying altitudes, pressures, or charges) such that fluid from the channels can travel in one direction only. In embodiments where it is desired that cells be physically separated, any mechanism can be used to isolate and separate cells.

In some embodiments, cultures without the patient's stromal cells (monoculture) and cultures with the patient's stromal cells (cis-coculture) are analyzed for target cell responses to agents in vitro in a patient-specific manner. Some embodiments of the invention relate to analysis of functional responses of primary patient cancer cells.

In some embodiments, the technology described herein is used to provide patient-specific care in a healthcare setting. In some embodiments, a healthcare provider obtains tissue samples from patients undergoing or beginning treatment with a pharmaceutical agent. In some embodiments, these samples are then separated based on one or more distinctive cell marker, cultured on a solid support, treated with one or more pharmaceutical agents, and observed for effectiveness using the methods, systems, and compositions described herein. The effectiveness results (e.g., the patient's cells are drug resistant or sensitive) are then used to tailor a patient's medical treatment. For example, if the analysis reveals that the patient is resistant to a drug, then the analysis may be repeated with alternative drugs until a drug is found to which that patient is sensitive.

In some embodiments, the systems and methods assists medical care providers in determining to which pharmaceutical agents a patient is sensitive or resistant. In some embodiments, healthcare providers consider a range of pharmaceutical agents, test the patient for resistance or sensitivity to a variety of these agents using the technology described herein, administer pharmaceutical agents to which the patient is sensitive according to the tests, follow up with the patient to ensure that the selected agent is working effectively, and re-test with the herein described technology if the effectiveness of the agent is not satisfactory.

EXAMPLE 1—Clinical Trials

A microscale cell culture and analysis device representing one embodiment of the invention was used to analyze CD138+ MM tumor cells' drug responses to the proteasome inhibitor bortezomib/Velcade and whether CD138− mononuclear cells from the same patient provide a protective effect. Cells were routinely cultured at 37° C. with 5% $CO_2$ in high-glucose DMEM containing 10% FBS, 100 U/mL penicillin, 100 µg/mL streptomycin (1% P/S), and 10 mM HEPES buffer at 1.0 to 1.5×105 cells/mL in tissue culture-treated flasks. A total of 5 μL of the concentrated cell suspension was dispensed by passive pumping into each microchamber.

Figure 2A:
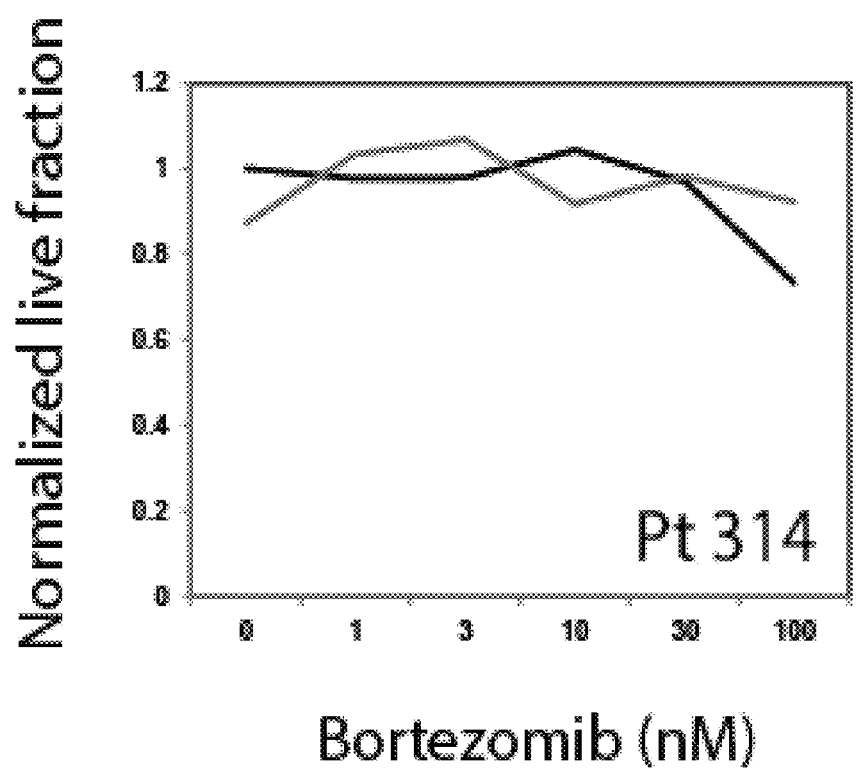
FIG. 2a-2r shows primary CD138+ multiple myeloma (MM) and CD138− mononuclear cells from patients that were co-cultured as in Example 1. Graphs show monoculture response in black and co-culture response in grey. All patients' in vitro responses matched their clinical response.
Figure 2B:
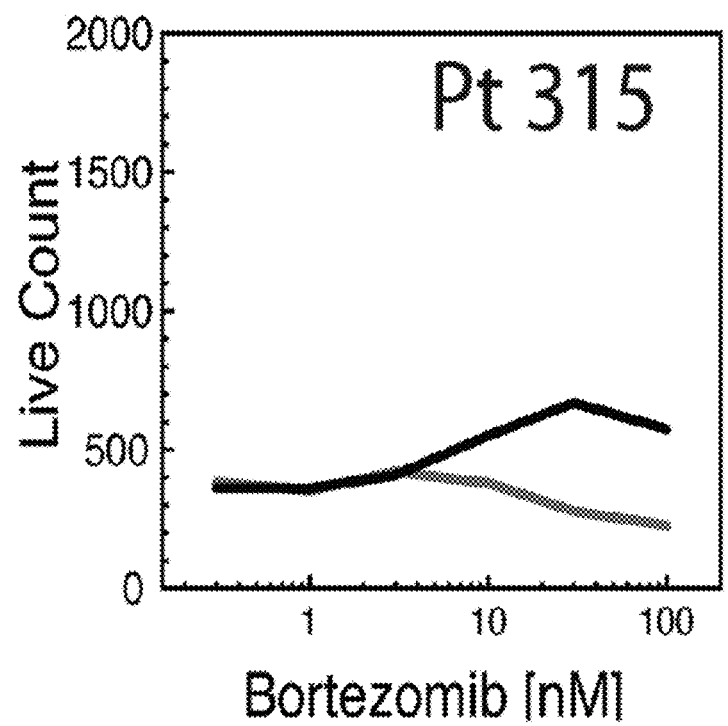
FIG. 2b shows results for patient 315.
Figure 2C:
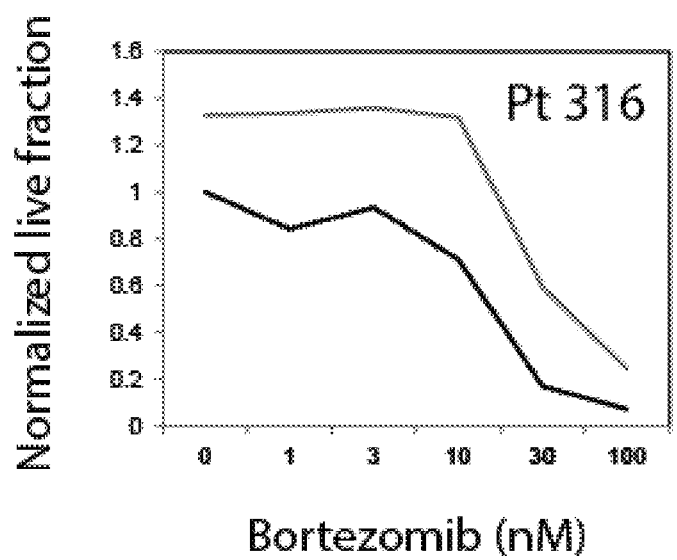
FIG. 2c shows results for patient 316.
Figure 2D:
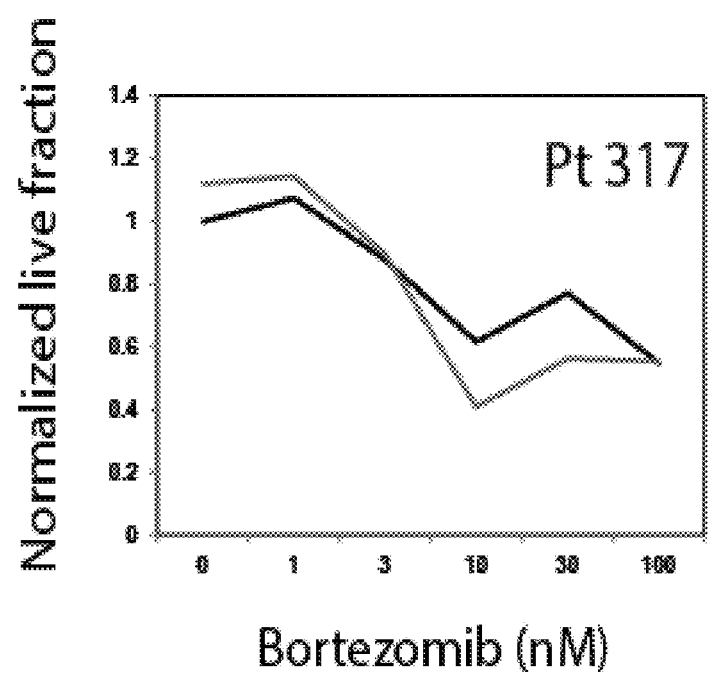
FIG. 2d shows results for patient 317.
Figure 2E:
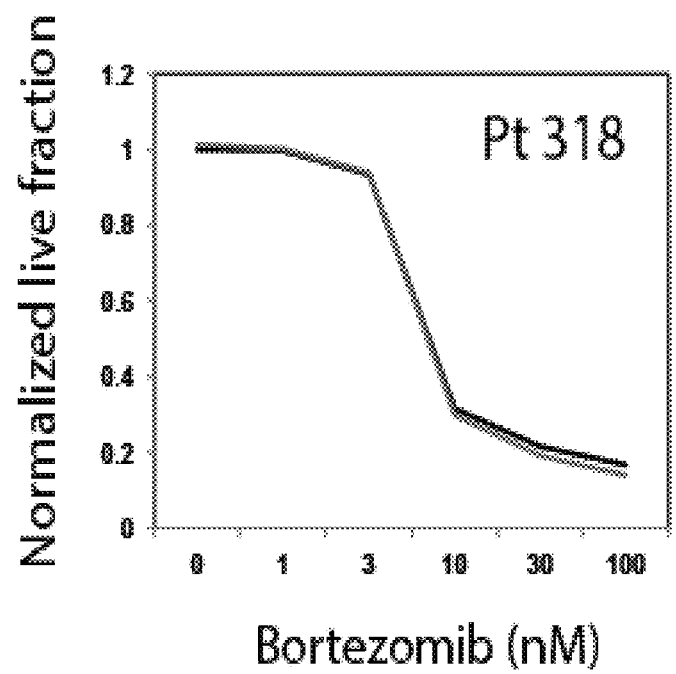
FIG. 2e shows results for patient 318.
Figure 2F:
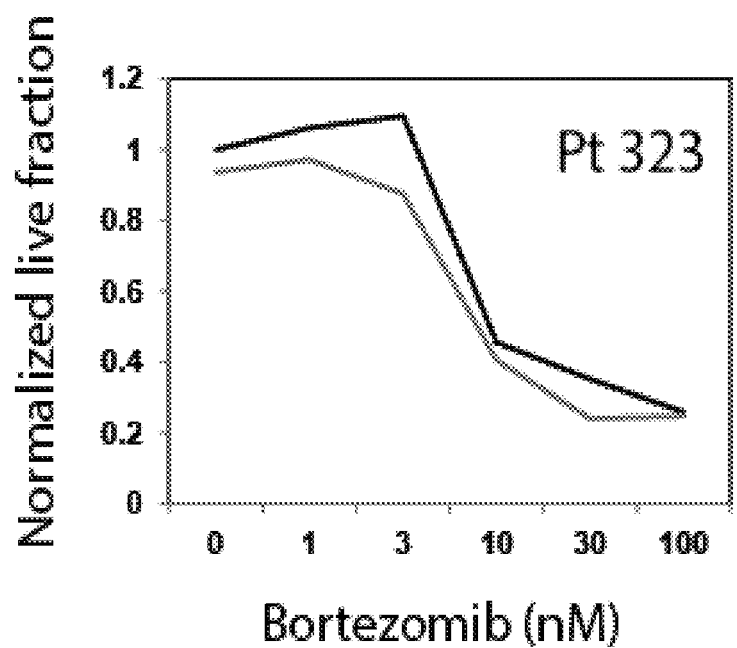
FIG. 2f shows results for patient 323.
Figure 2G:
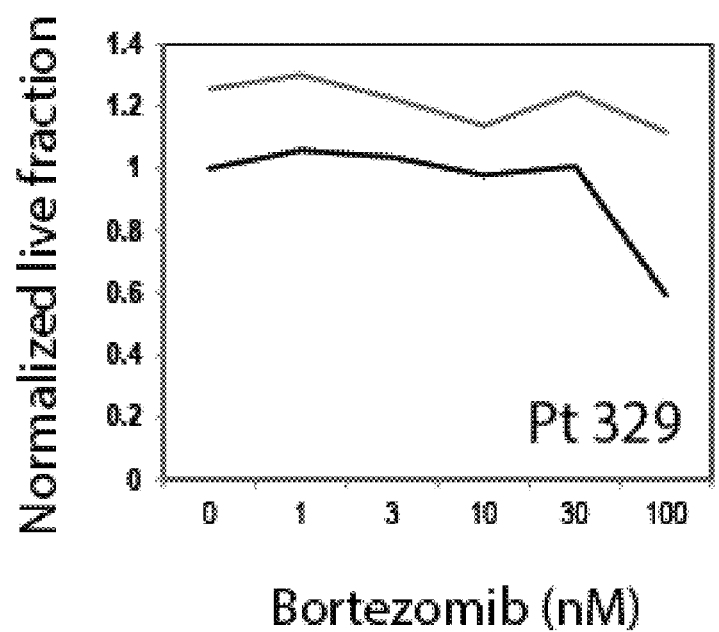
FIG. 2g shows results for patient 329.
Figure 2H:
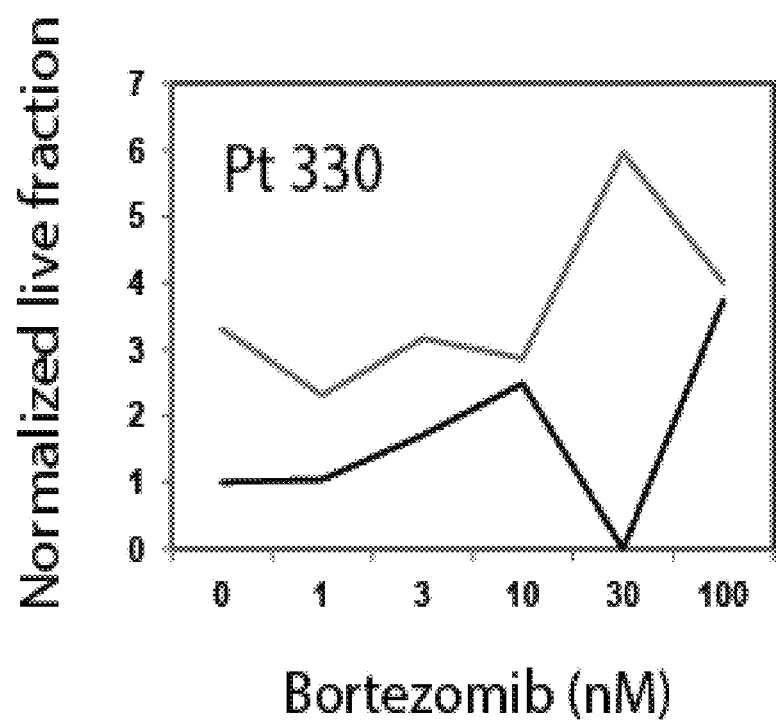
FIG. 2h shows results for patient 330.
Figure 2I:
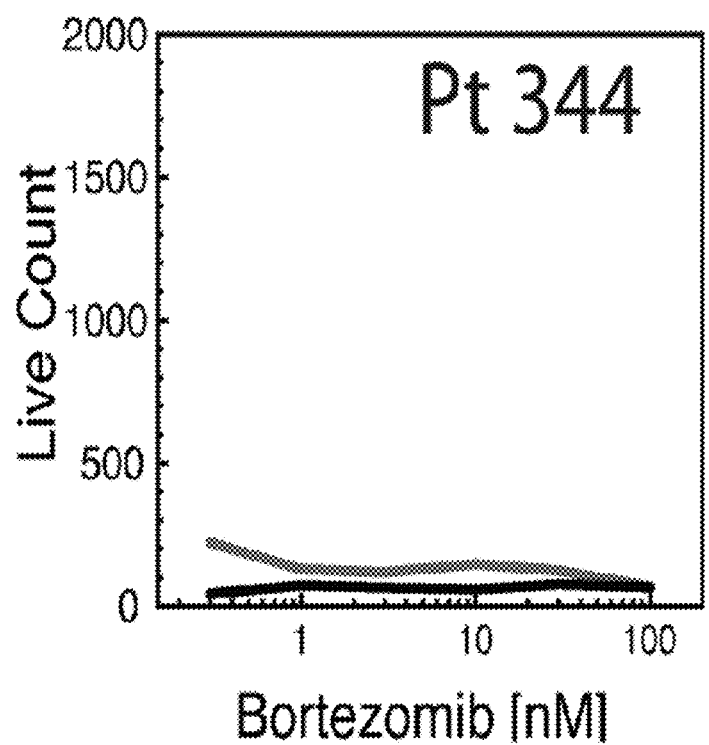
FIG. 2i shows results for patient 344.
Figure 2J:
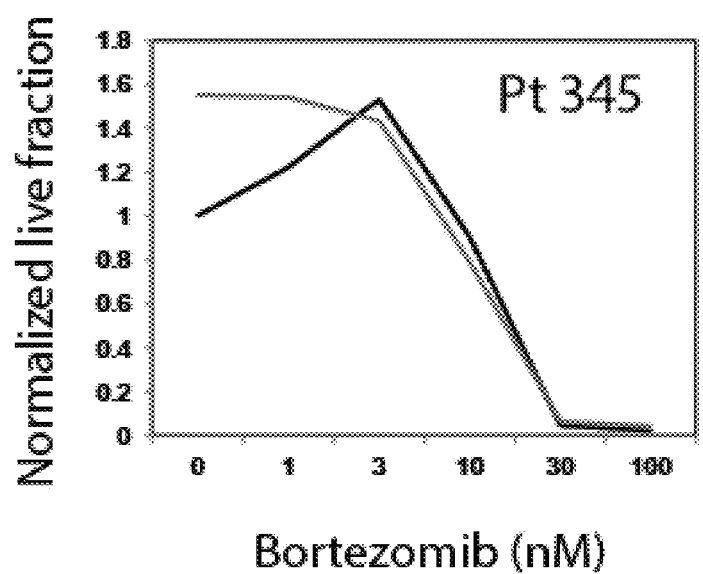
FIG. 2j shows results for patient 345.
Figure 2K:
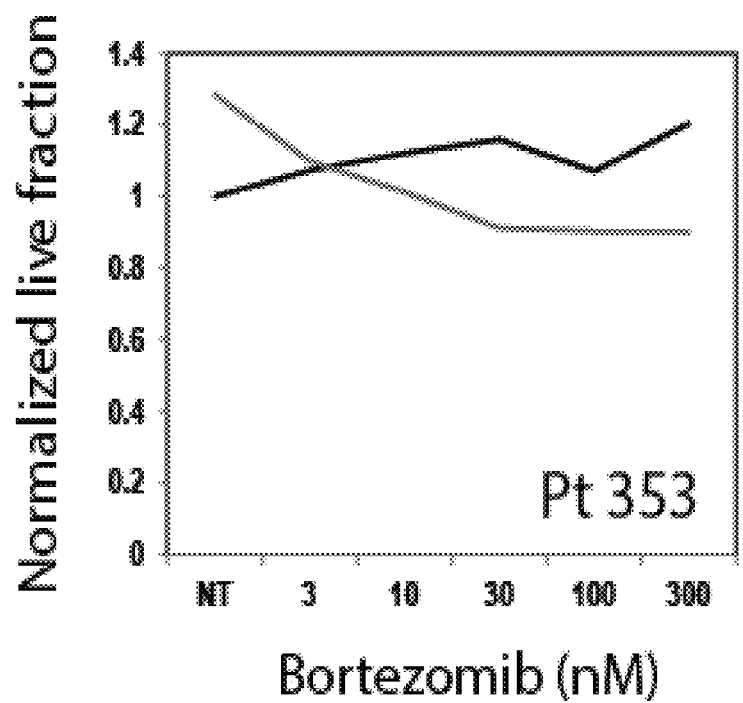
FIG. 2k shows results for patient 353.
Figure 21:
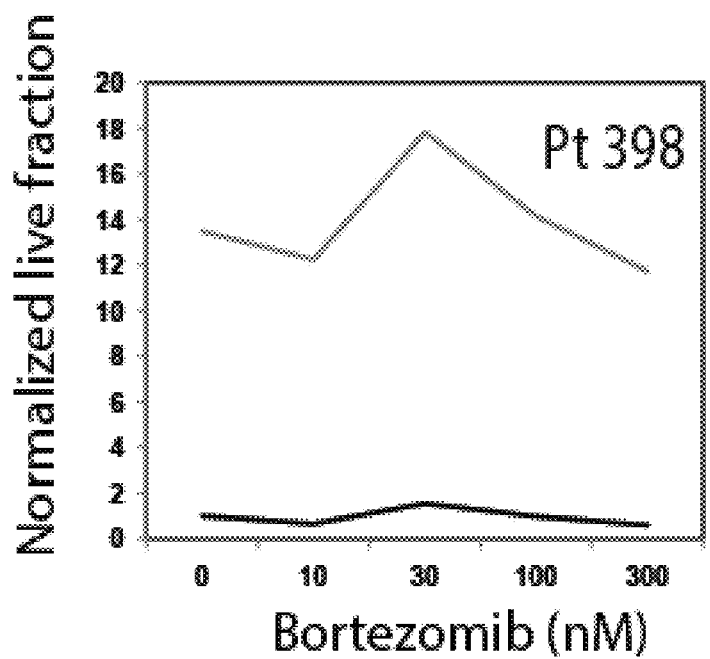
Figure 2M:
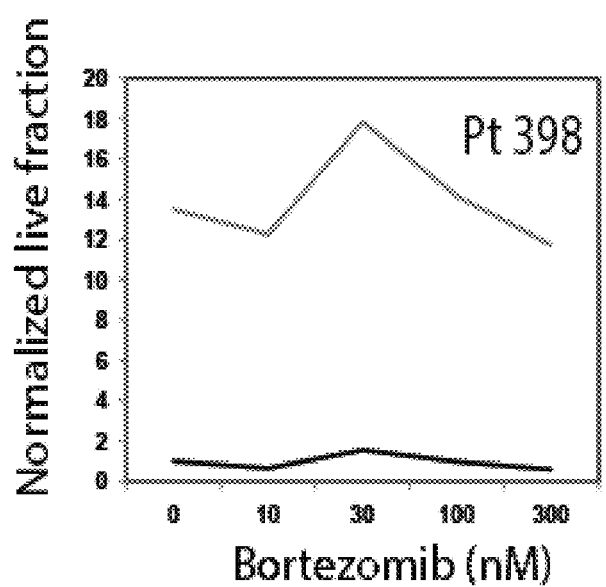
FIG. 2m shows results for patient 419.
Figure 2N:
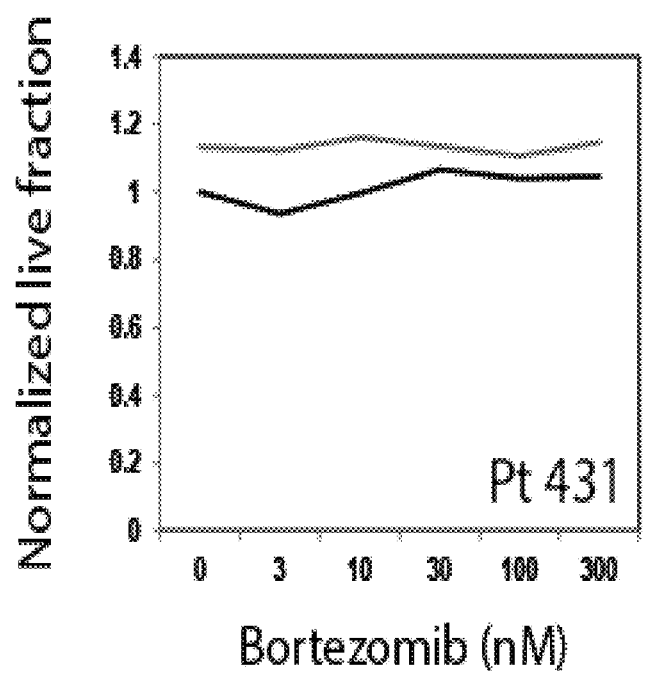
FIG. 2n shows results for patient 431.
Figure 2O:
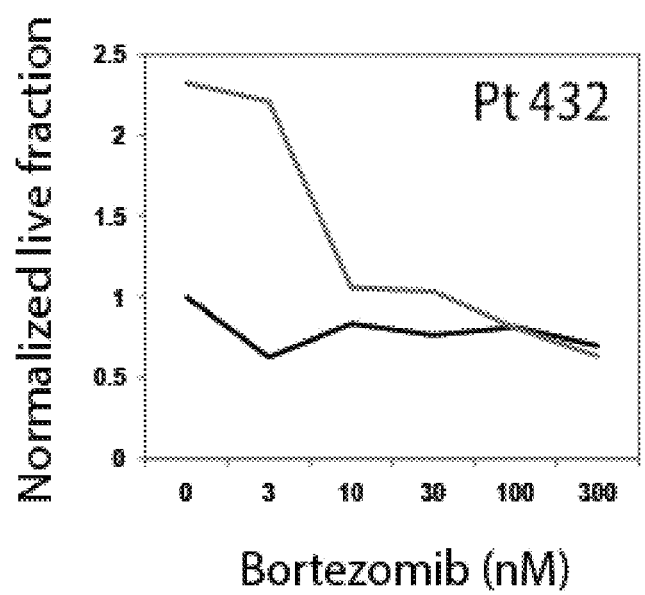
FIG. 2o shows results for patient 432.
Figure 2P:
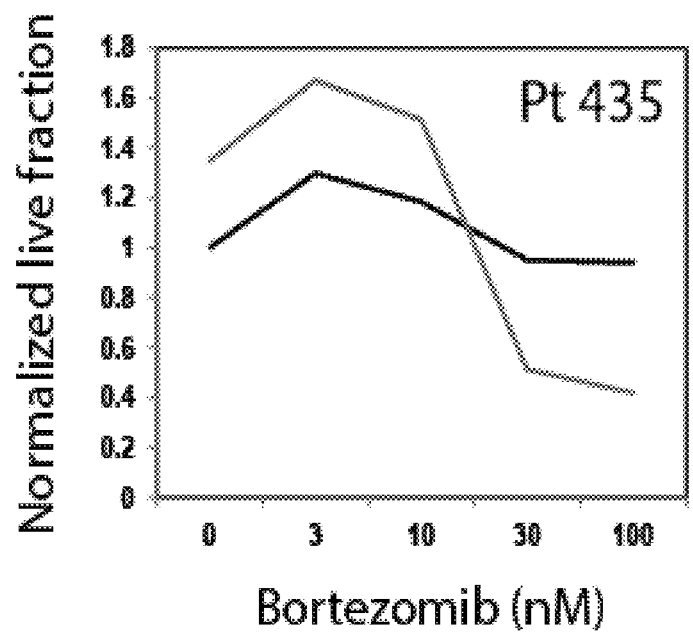
FIG. 2p shows results for patient 435.
Figure 2Q:
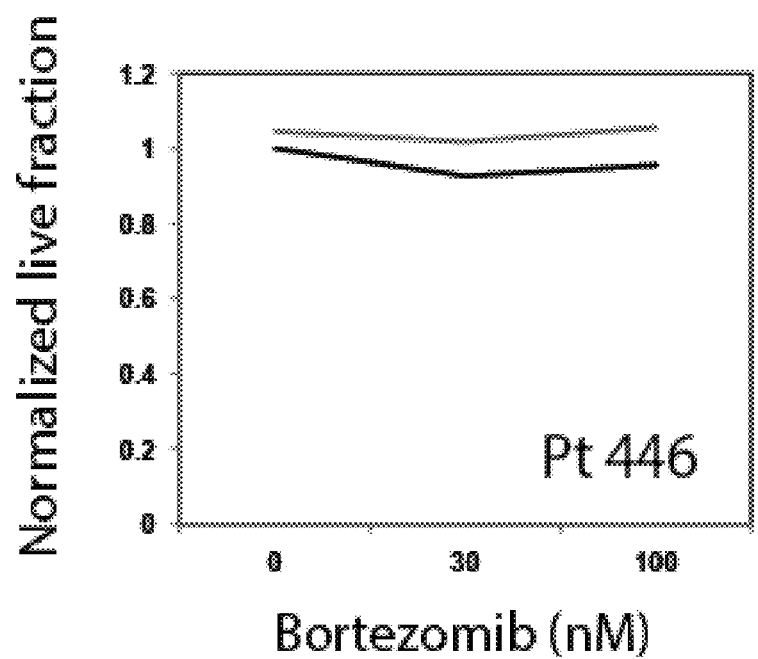
FIG. 2q shows results for patient 446.
Figure 2R:
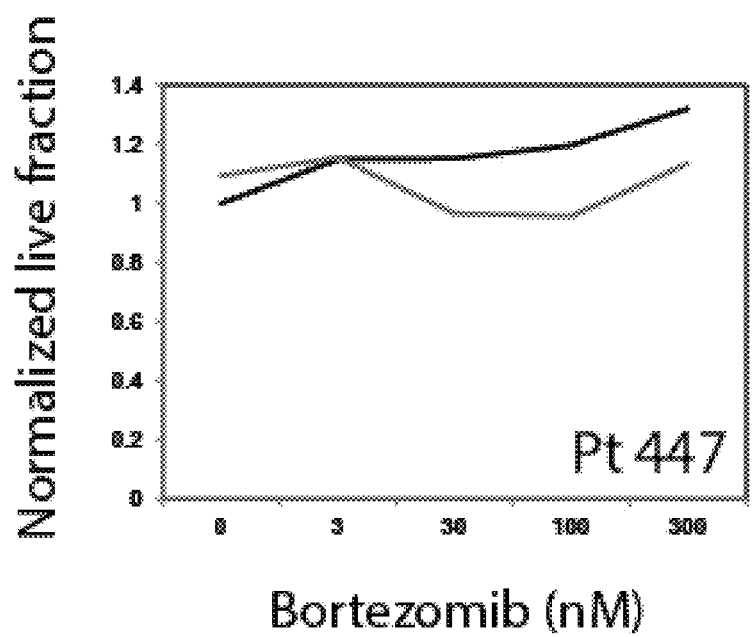

7500 CD138+ cells were added in a central well of a device resembling FIG. 1 with or without 8000 CD138− mononuclear cells in each side channel, which were obtained from the same patient bone marrow aspirates. Dose-dependent reductions in cell viability were obtained using calcein AM and ethidium homodimer staining for live and dead cells, respectively. Such MM cell viability was protected by the presence of patients' own CD138− mononuclear cells to varying degrees (FIGS. 2a-r). The blue line represents co-cultured conditions, while the black line represents the mono-cultured conditions. Patients 329, 316, and 318 are currently refractory to treatment and their co-cultured cells appear to show protection from bortezomib to varying degrees in comparison to their mono-cultured cells. Patients 315, 344, and 345 are currently sensitive to treatment and there appears to be no appreciable difference whether their cells are mono- or co-cultured. This analysis is not limited only to bortezomib and can be used to analyze other cancer drugs that are used to treat individual patients at different times in the treatment course (naïve, relapse, etc).

EXAMPLE 2—Predictive Assays

In some embodiments, the invention provides assays that predict patient-specific drug efficacy. Based on data gathered from cis-co-culture experiments and with the knowledge of the next treatment, the technology is used to treat patient cells in vitro with the drugs of the next treatment. This response is then matched to the patients' response in the clinic.

EXAMPLE 3—Cis-Co-Culture Benefits

Before the development of the present invention, there was no device, whether in macro- or micro-scale, that could culture patient myeloma cells with their own stromal cells (cis-coculture). Others isolate and expand different cell types in the stroma, such as bone marrow stromal cells (BMSCs), derived from different patient sources to co-culture with another patients' myeloma cells. This was avoided in the present technology for two reasons. First, the establishment of BMSCs amenable for conventional co-culture studies takes typically more than two weeks; however, myeloma cells only survive for a maximum of three days ex vivo. Therefore, one needs to cryopreserve myeloma cells while BMSCs are being generated in order to perform cis-co-culture studies. Cryopreservation of myeloma cells is often not efficient and may also alter the biology of the cell. Furthermore, only ~20% of the original frozen cells are viable when thawed. Thus, co-culture is classically performed in trans with BMSCs from one patient and myeloma cells from a different patient. Second, artificial enrichment for a specific cell type in the stroma, such as BMSCS, was avoided in the system; rather, all stromal mononuclear cells present in bone marrow aspirates obtained from individual patients were kept in their respective fractions that can vary from patient to patient.

EXAMPLE 4—Microscale Benefits

The number of myeloma cells obtained from individual patients can vary dramatically and be as low as $10^4$ cells per 10 ml aspirate. While certain macroscale cell death assays can work with low cell numbers to provide population-average responses to drugs, in some embodiments, the present invention is able to obtain individual cell responses within a population of cancer cells, as well as population-average responses, because data collection is performed at the single cell level. For example, in some embodiments, cell viability and protein subcellular localization within single cells is analyzed with image analysis consistent with EW Young's methods. Young, E W et al.: "Microscale functional cytomics for studying hematologic cancers" *Blood.* 2012 Mar. 8; 119(10).

EXAMPLE 5—Market Need

Multiple myeloma patients have many options for treatment but also the development of resistance is a common clinical problem. The current method of treatment selection is arbitrary and a more rational method is desperately needed. This invention provides a system for a laboratory assay to predict drug responses in individual patients. In some embodiments, the invention predicts what drugs patients will respond to in the clinic, by mimicking the microenvironment around the patient's malignancy as accurately as possible.

EXAMPLE 6—Device Preparation

The device was created according to methods described in Young E W et al., *Blood.* 2012 Mar. 8; 119(10) (hereby incorporated by reference in its entirety). Specifically, embodiments of the device are formed from polydimethylsiloxane (PDMS) that is sequentially bonded via plasma treatment to a glass slide. In some embodiments, the device is made of inert polymers, such as polystyrene to allow for analysis with hydrophobic molecules.

In some embodiments, the device used soft lithography techniques to fabricate single-use devices consisting of 12 independent microscale cell culture chambers (microchambers) arranged in a 3×4 array. Xia Y, "Soft Lithography" *Annu Rev Mater Sci.* 1998; 28:153-184. A channel layer master mold containing a central well, side chambers, diffusion ports, and an inlet and outlet channel were made. An additional master mold was made for the access port layer. Both layers were made of PDMS. The PDMS was mixed at a 10:1 base-to-curing agent ratio and cured at 80° C. for four hours. The two PDMS layers were sequentially bonded via plasma treatment to a glass slide to produce the final device.

EXAMPLE 7—Rapid Chemosensitivity and Chemoresistance Assay

The microfluidic platform shown in FIG. 1 was employed in this example. In short, by leveraging pressure differences at differently sized inlet and outlet ports, this platform was operated by passive pumping, requiring only a micropipet. Suspension cells were seeded through the inlet port of the central well and were allowed to settle overnight. Other cell types for coculture were seeded through the inlet ports of the side chambers. This system incorporates the following features: 1) capacity to be performed for all patients (e.g., 7500 cells per endpoint in the current study), 2) both tumor and non-tumor cells incorporated to mimic in vivo environment, and 3) simple and quick to perform without the need to extensively grow the cells in vitro. The entire assay requires only 3 days to complete. Patient MM cell viability within the microchannel during the 3 days was comparable to that of an MM cell line, RPMI8226, for 3 days.

After being freshly sorted within 24 hours of bone marrow aspiration, CD138$^+$ tumor cells were cultured in either mono-(MicroMC) or cis-coculture with the patients' own CD138$^-$ non-tumor mononuclear cell fractions (MicroC$^3$). Cryopreservation of MM tumor cells was avoided due to loss of viability of patient cells averaging only ~25% of cells being viable after thaw. The following day, the tumor cells were treated with varying doses of bortezomib, ranging from 0 to 300 nM (calculated final concentrations) for 24 hours. The bortezomib concentrations were varied from low to those higher than what is observed in patients (100 nM at peak plasma concentration) because the material used in microchannels, polydimethylsiloxane (PDMS), has the tendency to absorb hydrophobic molecules, and thus lower the effective concentration of drugs that are applied in culture. Due to the limited number of tumor cells obtained, some patient samples could not be analyzed for all bortezomib doses. After bortezomib treatment, the CD138$^+$ cells were stained with calcein AM and ethidium homodimer to count for live and dead cells, respectively.

After completion of the assay, live and dead cells were counted using an ImageJ-based in house software program (J'experiment). Due to the patient-to-patient variability of the retention of MM cells in the central chambers, live fractions for each dose were calculated and normalized to the 0 dose for both MicroMC and MicroC$^3$. The percent change in live fraction from the 0 nM to 100 nM dose of bortezomib for MicroMC and MicroC$^3$ was then calculated in order to classify patients' MM cell ex vivo responses. Patients whose CD138$^+$ cells did not survive in MicroMC but survived in MicroC$^3$ were omitted from MicroMC analysis.

Figure 3:
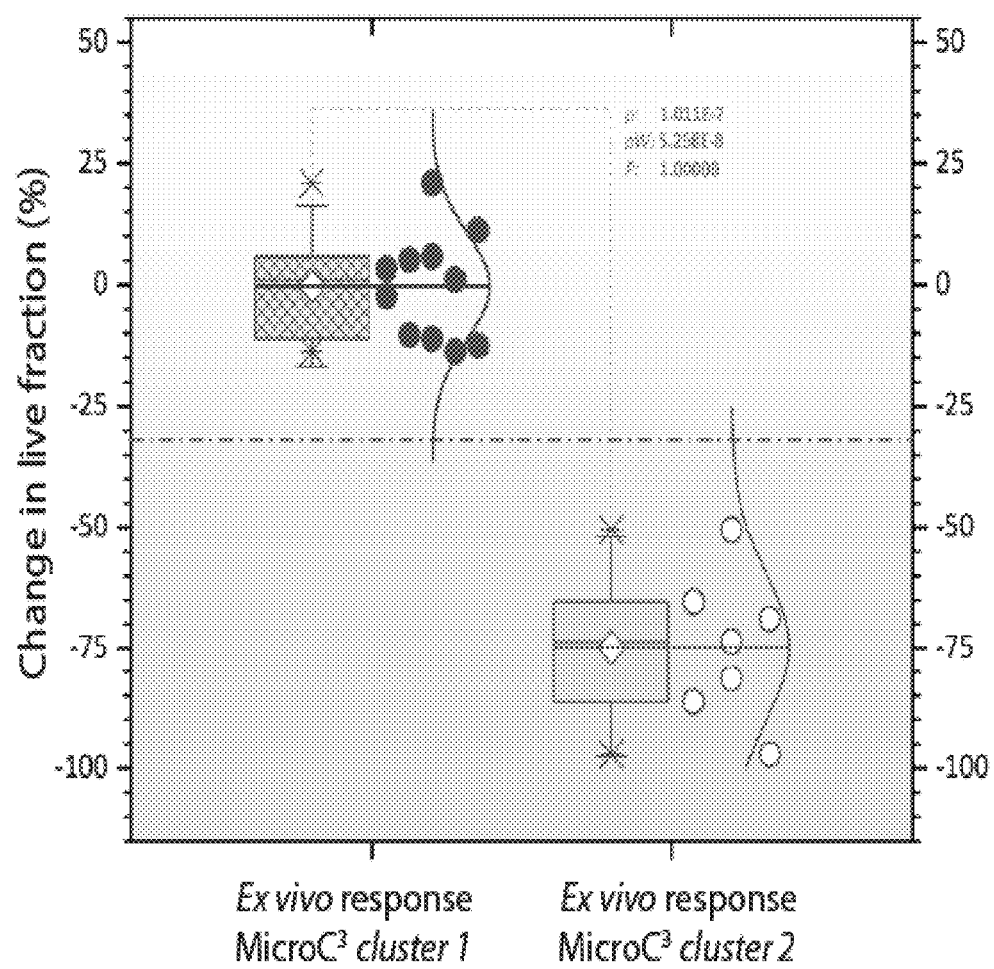
FIG. 3. Data from analyzed patient target cells exposed to drug as described in Example 7 were statistically analyzed.

Interestingly, ex vivo responses within MicroC$^3$ appeared to segregate into two groups, while responses within MicroMC did not (FIG. 3). Therefore, both the AIC (Akaike Information Criterion) and BIC (Bayesian Information Criterion) were calculated for unimodal, bimodal, and trimodal distributions for both MicroMC and MicroC$^3$. For MicroC$^3$ and at a clinically relevant treatment dose of 100 nM, a bimodal distribution of the response data was favored by the AIC as well as the BIC over unimodal and trimodal distributions. In contrast, none of these distributions was favored by AIC or BIC for the 100 nM treatment cases in MicroMC.

As both the AIC and BIC values indicated that a bimodal distribution was favored for MicroC$^3$, k-means and Gaussian mixture clustering methods were applied to segregate MicroC$^3$ ex vivo responses. For the 100 nM dose levels, k-means and Gaussian mixture clustering segregated 17 ex vivo responses in MicroC$^3$ into two clusters: 1—non-sensitive (10 cases), 2—sensitive (7 cases). The separation of the two resulting clusters ($p<10^{-5}$) was further in line with the Otsu threshold independently derived for the same data.

The ex vivo responses within MicroMC and MicroC$^3$ were then compared with the clinical responses of the same patients. The clinical characteristics of these patients are described in Table 1.

TABLE 1

| | | MicroMC | | | |
|---|---|---|---|---|---|
| Patient ID | Clinical response to Bortezomib | Ex vivo response [%] | kM cluster (k = 2) index | kM Silhouette value | GM cluster (k = 2) index |
| 314 | non-responder | −26.8 | 1 | 0.642 | 2 |
| 316 | responder | −92.8 | 2 | 0.873 | 2 |
| 317 | responder | −45.2 | 2 | 0.299 | 2 |
| 318 | responder | −83.4 | 2 | 0.894 | 2 |
| 323 | non-responder | n/a | n/a | n/a | n/a |
| 329 | non-responder | −40.8 | 2 | −0.022 | 2 |
| 330 | responder | −74.2 | 2 | 0.892 | 2 |
| 345 | responder | −97.8 | 2 | 0.856 | 2 |
| 353 | non-responder | 7.0 | 1 | 0.954 | 1 |
| 398 | non-responder | −1.6 | 1 | 0.959 | 1 |
| 402 | non-responder | n/a | n/a | n/a | n/a |
| 419 | non-responder | 17.7 | 1 | 0.927 | 1 |
| 431 | non-responder | 4.0 | 1 | 0.959 | 1 |
| 432 | responder | −18.8 | 1 | 0.837 | 1 |
| 435 | responder | −5.9 | 1 | 0.953 | 1 |
| 442 | non-responder | n/a | n/a | n/a | n/a |
| 446 | non-responder | −4.5 | 1 | 0.954 | 1 |
| 447 | non-responder | 19.6 | 1 | 0.919 | 1 |

AIC unimodal (k = 1) 156.681
AIC bimodal (k = 2) 156.591
AIC trimodal (k = 3) 157.407
BIC unimodal (k = 1) 158.097
BIC bimodal (k = 2) 160.131
BIC trimodal (k = 3) 163.071
Mean Silhouette (k = 2) 0.793

| | | MicroC$^3$ | | | |
|---|---|---|---|---|---|
| Patient ID | Clinical response to Bortezomib | Ex vivo response [%] | kM cluster (k = 2) index | kM Silhouette value | GM cluster (k = 2) index |
| 314 | non-responder | 5.8 | 1 | 0.935 | 1 |
| 316 | responder | −81.5 | 2 | 0.964 | 2 |
| 317 | responder | −50.5 | 2 | 0.736 | 2 |
| 318 | responder | −86.3 | 2 | 0.956 | 2 |
| 323 | non-responder | 21.0 | 1 | 0.923 | 1 |
| 329 | non-responder | −11.1 | 1 | 0.831 | 1 |
| 330 | responder | −73.6 | 2 | 0.965 | 2 |

TABLE 1-continued

| 345 | responder | −97.1 | 2 | 0.925 | 2 |
| 353 | non-responder | −10.3 | 1 | 0.841 | 1 |
| 398 | non-responder | 5.1 | 1 | 0.933 | 1 |
| 402 | non-responder | 62.4 | n/a | n/a | n/a |
| 419 | non-responder | −13.7 | 1 | 0.791 | 1 |
| 431 | non-responder | −2.3 | 1 | 0.909 | 1 |
| 432 | responder | −65.4 | 2 | 0.938 | 2 |
| 435 | responder | −68.9 | 2 | 0.954 | 2 |
| 442 | non-responder | 11.0 | 1 | 0.937 | 1 |
| 446 | non-responder | 1.0 | 1 | 0.924 | 1 |
| 447 | non-responder | −12.6 | 1 | 0.809 | 1 |

AIC unimodal (k = 1) 176.397
AIC bimodal (k = 2) 164.746
AIC trimodal (k = 3) 168.091
BIC unimodal (k = 1) 178.064
BIC bimodal (k = 2) 168.079
BIC trimodal (k = 3) 173.091
Mean Silhouette (k = 2) 0.898

All samples were collected and analyzed ex vivo without the prior knowledge of patients' clinical history to eliminate operator bias. The clinician determining responses was also blinded of the ex vivo response data. Remarkably, the MicroC$^3$ clusters separated by k-means and Gaussian mixture clustering into non-sensitive and sensitive were correctly identified as either clinically non-responsive or responsive. On the other hand, if the two clustering methods were applied to MicroMC, the results were much less clear. According to k-means, 12/15 (7/8 non-sensitive and 5/7 sensitive) monocultured ex vivo patient responses matched their respective clinical responses. According to Gaussian mixture clustering, only 11/15 (6/8 non-sensitive and 5/7 sensitive) monocultured ex vivo patient responses matched their respective clinical responses.

These results were further supported when the clustering methods were applied to the changes in live fraction from 0 to 30 nM of bortezomib treatment. MicroC$^3$ successfully identified 16/16 ex vivo responses, while MicroMC identified 12/15 at this dose of bortezomib. Thus, patients' CD138$^+$ MM cells in MicroC$^3$ appear to more uniformly respond to bortezomib (either sensitive or non-sensitive) compared to the same cells analyzed alone without the influence of CD138$^-$ cell population.

One anomalous patient, Pt 402, was removed from the above analyses. Pt 402's CD138$^+$ cells showed no response to bortezomib ex vivo and the subject's clinical response was non-responsive. However, when included in the clustering analyses, trimodal distributions were favored with Pt 402's ex vivo responses being classified as a third cluster. Peculiarly, Pt 402 was the only patient with a t(14;16) translocation affecting c-Maf oncogene with a very poor prognosis that occurs in ~5% of MM patient. It is contemplated that patients with a t(14;16) translocation, or patients with an ex vivo response similar to Pt 402, do comprise a third cluster of patients displaying ex vivo growth response to bortezomib.

Pt's 317, 318, and 323 were newly diagnosed patients and their tumor cells showed sensitivity to bortezomib in MicroC$^3$ assay. These patients then went on bortezomib-containing regimens without the clinician's prior knowledge of the ex vivo responses. Clinically, Pt. 317 and 323 had a partial response, and Pt. 318 showed a complete response to bortezomib-containing regimens. Similarly, Pt. 316's tumor cells showed sensitivity to bortezomib in MicroC$^3$ assay but the patient was classified as refractory to treatment with lenalidomide and dexamethasone at the time of the biopsy. This patient then went on bortezomib-containing therapy and had a partial response. In contrast, Pt. 442 was a newly diagnosed patient whose tumor cells did not respond to bortezomib in MicroC$^3$. This patient then went on a bortezomib-containing regimen, again without the clinician's prior knowledge of the ex vivo data, and did not respond clinically. Therefore, patient's CD138$^+$ cell response to bortezomib in the MicroC$^3$ system predicts patients' clinical response to bortezomib-containing therapy.

These results demonstrate several important features. First, the MicroC$^3$ requires only several thousands of CD138$^+$ cells per condition for functional analysis, thereby enabling the analysis of MM cell responses in virtually all patient bone marrow aspirate samples. This may avoid a potential bias towards samples with larger numbers of tumor cells, which could be unintentionally incorporated when certain assays such as biochemical ones that require a larger starting cell number are used to analyze primary patient samples. Second, both tumor and non-tumor cells are incorporated into the design of MicroC$^3$ to recapitulate in vivo environment. Given that tumor-associated cell types can have significant impacts on tumor cell drug responses, incorporation of these non-tumor cell populations without artificial enrichment of individual cell components allows tumor cells to behave more similarly to in vivo conditions than when they are cultured alone. Additionally, the MicroC$^3$ assay is simple and quick to perform taking only three days from the sample acquisition to the analysis of the cell responses, negating the need for culturing and passaging of the patient cells. Incorporation of total CD138$^-$ cell population is contemplated to enable ex vivo recapitulation of the tumor cell to non-tumor cell interactions in the cancer microenvironment. Because MicroC$^3$ is performed with freshly isolated tumor and non-tumor cells, passaging and potential enrichment of the CD138$^+$ tumor cell subpopulations are also avoided. Furthermore, in some embodiments, MicroC$^3$ is conducted at the microscale, using fluid volumes of 10 μL in the central chamber and 5 μL in each of the side chambers. These low fluid volumes are contemplated to concentrate important soluble factors produced by both the tumor and non-tumor companion cells which may otherwise be diluted in conventional culture conditions (e.g., Transwell cultures).

While all other previous Chemosensitivity-resistance Testing systems (CSRAs) also categorize patients into high and low response groups, MicroC$^3$ is the only CSRA that has utilized clustering methods to segregate and identify ex vivo patient responses without operator bias. Remarkably, these clustering methods have identified 7 out of 7 patients whose MM cells were sensitive in MicroC$^3$ were either currently clinically responsive to bortezomib-containing therapy or went on to respond to bortezomib-containing therapy after the treating clinician selected this treatment. Moreover, 10 out of 10 patients with the MicroC$^3$ non-sensitive designation were either currently relapsed and/or refractory to bortezomib-containing therapy or did not respond to subsequent bortezomib-containing therapy. In comparison, when the same primary MM cells were cultured under the same conditions but without the influence of the CD138$^-$ cell fractions, the agreement between ex vivo and clinical responses were much less evident. It should be mentioned that the microchannel-based monoculture assay, MicroMC, was still able to match a large percentage (80%) of ex vivo responses to clinical responses, which is comparable or better than other CSRAs tested for other cancer types that have garnered ~30-60% accuracy (see e.g., S. Ugurel et al., *Clin. Cancer Res.* 12, 5454-63 (2006); T. H. Lippert, H.-J. Ruoff, M. Volm, *Int. J. Med. Sci.* 8, 245-53 (2011); and M. Suggitt, M. C. Bibby, *Clin Cancer Res* 11, 971-981 (2005)).

Figure 4:
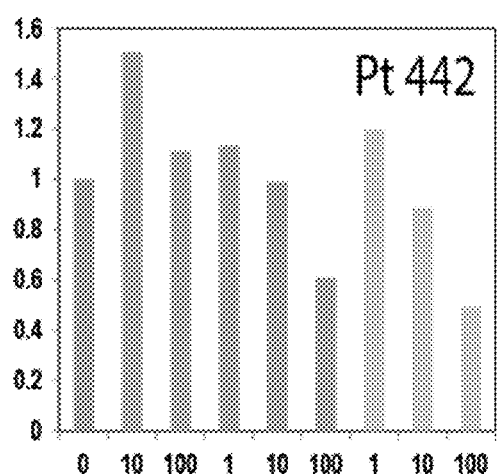
FIG. 4. Patient 442 was tested for sensitivity against a plurality of therapeutic agents (bortezomib, lenalidomide, and pomalidomide). Patient 442's MM cells exhibited resistance to bortezomib in vitro but sensitivity to lenalidomide and pomalidomide. Clinically, Patient 442 was initially treated with a bortezomib-containing regimen but did not respond. Patient 442 then was treated with a lenalidomide-containing regimen and had a partial response.

A predictive CSRA that enables stratification of patients prior to specific therapy allows patients to avoid ineffective therapies as well as unnecessary cost associated with such therapies. Additional therapeutic agents (carfilzomib, lenalidomide, and pomalidomide) were also tested in a small number of cases and MicroC$^3$ was able to categorize patients into sensitive and non-sensitive groups. For example, FIG. 4 shows data obtained with patient 442 using bortezomib, carfilzomib, lenalidomide, and pomalidomide.

Materials and Methods

Microchannel Fabrication and Preparation

Single-use devices comprised of 12 or 24 cell culture chambers were fabricated using soft lithography using two master molds established previously (Y. Xia, G. M. Whitesides, *Annu. Rev. Mater. Sci.* 28, 153-184 (1998); Duffy, J. McDonald, O. Schueller, G. Whitesides, *Anal. Chem* 70, 4974-4984 (1998)). Polydimethylsiloxane (PDMS) was mixed at a 10:1 base:curing agent ratio, poured on the master molds, and cured at 80° C. for 4 hrs. Two separate PDMS layers were made, one for the channel layers containing the central well, side chambers, diffusion ports, and inlet and outlet channels, and one for the access port layer. The two PDMS layers were then soxhlet extracted and plasma treated to bond to a glass slide. The final device was then baked at 120° C. for 15 min to increase bond strength and release any bubbles.

Before cell culture, the chambers on the device were filled first with 70% ethanol as a wetting agent as well as a disinfectant. The ethanol was rinsed with 3 volume replacements (VRs) of 1× phosphate-buffered saline (PBS). The 1×PBS was then replaced with 3 VRs of the appropriate cell culture medium. The final such prepared device can be stored up to 3 weeks in a 37° C. incubator when encased with appropriate humidifying and sterile conditions. If stored longer than 24 hours, the media is replaced with 1 VR of fresh media prior to cell culture.

Cell Line Culture and Preparation

RPMI8226 (human MM cell line) was obtained from ATCC. RPMI8226 cells (1.0 to 1.5×10$^5$ cells/mL seeding density) were routinely cultured at 37° C. with 5% CO$_2$ in high-glucose Dulbecco's modified eagle's medium (DMEM) containing 10% fetal bovine serum (FBS), 100 U/mL penicillin, 100 g/mL streptomycin (1% P/S), and 10 mM hydroxyethyl piperazineethanesulfonic acid (HEPES) in tissue culture-treated flasks. Cells were passaged every 2 to 3 days. For experiments conducted in microchambers, RPMI8226 cells were collected and resuspended at 1.0×10$^6$ cells/mL of fresh growth media. A total of 5 µL of the concentrated cell suspension was dispensed by passive pumping into each microchamber.

Primary Patient Cell Culture and Preparation

Bone marrow aspirates (5-10 ml each) were obtained with informed consent from patients diagnosed with multiple myeloma. Clinical status of the patients was determined by International Myeloma Working Group (IMWG) criteria (N. C. Munshi et al., *Blood* 117, 4696-4700 (2011)). 'Sensitive or Responsive' is defined as patient achieving at least a partial remission/response. 'Relapsed' is defined as patient having ≥0.5 g/dl increase in monoclonal protein or >200 mg in 24 hours in urine light chains after obtaining at least a partial remission. 'Refractory or Resistant' is defined as patient having progressed on or within sixty days of treatment. Relapsed and/or refractory patients were defined as non-responsive patients for the purpose of this assay. The researcher assessing clinical statuses of the patients was blinded to assay results and separate from the staff performing the assay. The ex vivo data and the clinical statuses were only compared after the assay was completed.

Aspirate volumes were doubled with Iscove's Modified Dulbecco's Medium (IMDM)+100 units/mL heparin (Sigma-Aldrich). They were doubled again with IMDM+10 units/mL DNAseI (Roche). After rocking at room temperature for 30 minutes, 2 volumes of cell mixture were put over 1 volume of lymphocyte separation medium (Cellgro) and centrifuged for 35 minutes at 200 g. The interface and 2-3 mLs of the buffy coat layer were taken, and rinsed with PBS+2 mM ethylenediaminetetraacetic acid (EDTA). At this point, the total mononuclear cells were either sorted or cryopreserved with cryopreservation medium (90% FBS, 10% DMSO). CD138$^+$ magnetic MACS® beads (Miltenyi Biotec) were used to positively sort for multiple myeloma cells per the manufacturer's instructions to >95% purity as determined by fluorescence-activated cell sorting (FACS). For sorting with cryopreserved samples, the sample was quickly thawed at 37° C., resuspended in 10 mLs of DMEM and 20% FBS and pelleted to remove DMSO. The sample was then incubated in high glucose DMEM containing 20% FBS and 1% P/S and 10 mM L-glutamine with the addition of DNAseI for 1 hour with agitation approximately every 15 min to break up cell clumps. The sorting protocol was then followed as above with the CD138$^+$ MACS beads.

For microchannel experiments, CD138$^+$ cells were resuspended in high glucose DMEM containing 20% FBS and 1% P/S and 10 mM L-glutamine at a density of 1.5×10$^6$/mL and 5 µL were seeded into the inlet port of each central well for a total of 7500 cells. For coculture experiments, CD138$^-$ cells were resuspended at a density of 4×10$^6$ cells/mL in the same media as the CD138$^+$ cells and 2 µL were seeded into the inlet port of each side channel for a total of 8000 cells on each side. After an overnight culture, fresh media containing varying concentrations of drug were added to the input port, resulting in exposures of both MM cells and non-MM cells in the side chambers at the final concentrations needed. If the number of cells permitted, duplicates of drug dose conditions were performed. Cultures were treated with the drug for 24 hrs after which live and dead cells were stained, respectively, as described below.

Reagents

Bortezomib (PS-341 or Velcade) and carfilzomib (Krypolis) were obtained as a 2.6 mM clinical saline solution and stored at −80° C. in separate aliquots. The drugs were thawed 5 minutes before each treatment, serially diluted to the desired concentrations in media warmed to 37° C., and dispensed into microchambers in 3 sequential VRs followed by aspiration of the outlet port to reach desired final concentrations. Lenalidomide and pomalidomide (Revlimid and Pomalyst, respectively) were purchased from Selleck Chemicals and reconstituted in DMSO to a stock concentration of 100 μM and stored at −80° C. These chemicals were thawed, serially diluted, and dispensed into microchambers in the same manner as bortezomib. LIVE/DEAD Viability/Cytotoxicity Assay Kit from Invitrogen was used to detect live and dead cells in microchambers. Both calcein AM (green) and ethidium homodimer (red) were used at a working concentration of 4 μM.

Immunofluorescence Image Analysis

Cells were stained with LIVE/DEAD for 10 min, and washed with one VR of fresh media. All fluorescent images were taken with a Nikon Eclipse Ti inverted fluorescent microscope coupled to a Nikon DS-Qi1Mc CCD camera (Nikon Instruments Inc., Melville, N.Y., USA) at a magnification of 4×. Image analysis was performed in ImageJ with custom in-house algorithms and database management to count live and dead cells (J'experiment) (E. W. Young et al., Microscale functional cytomics for studying hematologic cancers, *Blood* 119, e76-85 (2012)).

Statistical Analysis

Monocultured live fraction responses to bortezomib were normalized to the monoculture 0 dose; cis-cocultured live fraction responses to bortezomib were normalized to the coculture 0 dose. The changes in live fractions as a response to 30 nM and 100 nM doses of bortezomib were calculated. The mean, standard deviation, median, interquartile range (IQR), and Otsu threshold (T. Kurita, N. Otsu, N. Abdelmalek, *Pattern Recognit.* 25, 1231-1240 (1992)) were calculated for both monoculture and cis-coculture responses in Matlab (MathWorks, Nattick, Mass.) and graphed using Origin (OriginLab, Northampton, Mass.).

Clustering Analysis of Ex Vivo Data

In order to automatically identify potential distinct subpopulations in an unsupervised fashion and with high discriminative power, ex vivo data were separated using both k-means clustering (J. a Hartigan, M. a Wong, *J. R. Stat. Soc.* 28, 100-108 (1979)) and Gaussian mixture (GM) modeling (G. McLachlan, D. Peel, *Finite Mixture Models* (2000; doi (dot) wiley (dot) com/10.1002/0471721182), p. 419.) algorithms. We chose to compare both methods for robustness. In both methods, the data set is iteratively partitioned into k clusters by minimizing the within-cluster variance while maximizing the between-cluster variance. Clustering of the ex vivo response data was carried out using the Statistics Toolbox of Matlab (MathWorks, Nattick, Mass.). The degree of dimensionality (i.e., the numbers of clusters) was determined by a) maximizing the mean Silhouette index of the k-means clusters and by b) minimizing the Akaike and Bayesian information criterion (AIC and BIC, respectively) of the Gaussian mixture model.

We claim:

1. A method for cellular analysis comprising:
    (a) placing hematological cancer cells isolated from a patient on a solid support;
    (b) placing non-cancerous mononuclear cells comprising bone marrow stromal cells isolated from the same patient in a different region of said solid support and in fluidic connection with the cancer cells;
    (c) contacting the cancer cells and/or non-cancerous cells with an agent; and
    (d) measuring an effect or lack of effect of the agent on the cancer cells and/or non-cancerous
wherein the cellular analysis is completed within four days of isolation of both the cancer cells and the non-cancerous cells from the patient.

2. The method of claim 1, wherein said placing the non-cancerous mononuclear cells comprising bone marrow stromal cells comprises placing the non-cancerous mononuclear cells in a portion of the solid support not occupied by the cancer cells.

3. The method of claim 1, wherein the cancer cells are multiple myeloma cells.

4. The method of claim 1, wherein the solid support is a chip, dish, bead, scaffold, or gel.

5. The method of claim 1, wherein the agent is a drug.

6. The method of claim 5, wherein the effect of the drug on the cancer cells indicates which drug(s) to administer to the patient.

7. The method of claim 1, wherein the agent is a chemotherapeutic agent.

8. The method of claim 1, wherein the agent is a candidate chemotherapeutic agent.

9. The method of claim 1, further comprising the step of administering to the patient the agent measured to have an effect in step (d).

10. The method of claim 1, further comprising the step of reporting to a health care worker an identity of an agent likely to be therapeutically effective for said patient.

11. The method of claim 1, wherein the solid support comprises two or more separate regions that are fluidically connected through channels with dimensions no greater than 300 μm wide and 70 μm deep.

12. The method of claim 1, wherein said agent is bortezomib.

13. The method of claim 1, wherein said cancerous cells are CD138+ cells.

14. The method of claim 1, wherein said non-cancerous cells are CD138− cells.

15. The method of claim 1, wherein the cancer cells and non-cancerous cells are isolated from the same bone marrow aspirate.

16. The method of claim 1, wherein about $7.5 \times 10^3$ cancer cells are placed on the solid support.

17. The method of claim 1, wherein about $1.6 \times 10^4$ non-cancerous cells are placed on the solid support.

18. The method of claim 1, wherein the cellular analysis indicates that the patient will be responsive to said agent.

19. The method of claim 1, wherein the cellular analysis indicates that the patient will be non-responsive to said agent.

20. The method of claim 1, wherein the cellular analysis indicates that the agent will be a therapeutically effective agent for a patient.

21. The method of claim 1, wherein the cellular analysis indicates that the patient will exhibit drug resistance to the agent.

* * * * *

UNITED STATES PATENT AND TRADEMARK OFFICE
CERTIFICATE OF CORRECTION

PATENT NO. : 9,958,432 B2
APPLICATION NO. : 14/491701
DATED : May 1, 2018
INVENTOR(S) : Chorom Pak et al.

It is certified that error appears in the above-identified patent and that said Letters Patent is hereby corrected as shown below:

Column 20, Line 4, Claim 1 replace:
"(d) measuring an effect or lack of effect of the agent on the cancer cells and/or non-cancerous wherein the cellular analysis is completed within four days of isolation of both the cancer cells and the non-cancerous cells from the patient."

With:
--(d) measuring an effect or lack of effect of the agent on the cancer cells and/or non-cancerous cells, wherein the cellular analysis is completed within four days of isolation of both the cancer cells and the non-cancerous cells from the patient.--

Signed and Sealed this
Fourth Day of September, 2018

Andrei Iancu
*Director of the United States Patent and Trademark Office*